United States Patent [19]

Croce et al.

[11] 4,046,821

[45] Sept. 6, 1977

[54] OXYCHLORINATION OF HYDROCARBONS IN THE PRESENCE OF NON-HALIDE COPPER CONTAINING CATALYSTS

[75] Inventors: Louis J. Croce, Seabrook, Tex.; Laimonis Bajars, Princeton; Maigonis Gabliks, Highland Park, both of N.J.

[73] Assignee: Petro-Tex Chemical Corporation, Houston, Tex.

[21] Appl. No.: 576,589

[22] Filed: May 12, 1975

Related U.S. Application Data

[63] Continuation of Ser. No. 889,671, Dec. 31, 1969, abandoned.

[51] Int. Cl.² .............................. C07C 17/15
[52] U.S. Cl. ........................... 260/654 A; 260/650 R; 260/651 R; 260/655; 260/656 R; 260/659 A; 260/662 A; 252/437; 252/438; 252/439; 252/462
[58] Field of Search .......... 260/650 R, 651 R, 654 A, 260/655, 656 R, 659 A, 662 A

[56] References Cited

U.S. PATENT DOCUMENTS

| 3,210,431 | 10/1965 | Engel | 260/659 A |
| 3,427,359 | 2/1969 | Rectenwald et al. | 260/659 A |
| 3,657,367 | 4/1972 | Blake | 260/659 A |

FOREIGN PATENT DOCUMENTS

| 1,104,661 | 2/1968 | United Kingdom | 260/656 R |

*Primary Examiner*—Charles F. Warren
*Attorney, Agent, or Firm*—Kenneth H. Johnson

[57] ABSTRACT

Copper chloride has been employed as a reagent for oxychlorination of hydrocarbons. It has now been found that a non-halide copper compound in combination with a rare earth compound is an excellent oxychlorination catalyst, e.g. a $CuCO_3$ - $CeO_2$ catalyst calcined at 900° C. for 1 hour converted 99 mole % of ethylene fed at a selectivity of 100% to chlorinated products, principally vinyl chloride, ethyl chloride and dichloroethane.

24 Claims, No Drawings

OXYCHLORINATION OF HYDROCARBONS IN THE PRESENCE OF NON-HALIDE COPPER CONTAINING CATALYSTS

This is a continuation of application Ser. No. 889,671 filed Dec. 31, 1969 now abandoned.

The present invention relates to a catalyst and process for oxychlorination of hydrocarbons.

This invention is applicable to the chlorination of paraffins, olefins, cycloolefins, acetylenes and aromatics. The term oxychlorination as used herein refers to a reaction in which the source of chlorine employed for the chlorination is gaseous hydrogen chloride which is made to give up its chlorine in useful form. Copper chloride with various modifiers has been employed to react with hydrogen chloride to make it give up its chlorine through a series of well known reactions. If it is considered that the copper chlorides employed in the prior art oxychlorinations of hydrocarbons are true reagents rather than catalysts, as is generally accepted, then the various chlorides involved in those reactions can be represented in the following typical reaction $$Cu_2Cl_2 + 1/2 O_2 \rightarrow CuO \cdot CuCl_2 \qquad 1$$

$$CuO \cdot CuCl_2 + 2HCl \rightarrow 2CuCl_2 + H_2O \qquad 2$$

$$2CuCl_2 + RH \rightarrow RCl + Cu_2Cl_2 + HCl \qquad 3$$

It is recognized that each of these reactions has different thermal requirements and characteristics from each of the others. The various solutions proposed have sought to find a compromise set of conditions for these diverse reactions.

The present invention provides a solution to the problems encountered with copper chloride by using a novel catalyst system. Briefly stated, one aspect of the present invention is a catalyst for use in oxychlorination of hydrocarbons comprising a non-halide copper component and a rare earth component. Another aspect of the present invention is an improvement in the process of oxychlorination of hydrocarbons wherein the improvement comprises using a catalyst comprising a non-halide copper component and a rare earth component.

The non-halide copper component can contain other elements in addition to copper, for example, a preferred group of elements is selected from the group consisting of oxygen, sulfur, nitrogen, phosphorus, arsenic, tin, lead, iron, chromium, molybdenum, tungsten, vanadium, titanium and mixtures thereof. Suitable copper compounds would include copper oxide, copper sulfate, copper nitrate, copper phosphate, copper arsenate, copper stannate, copper plumbate, copper ferrite, copper chromate, copper molybdate, copper tungstate, copper vanadate and copper titanate.

The rare earth component of the present oxychlorination catalysts acts as a promoter for the copper component. Although it has been found that the atomic ratio of rare earth promoter to copper can vary widely without detriment to the catalytic effect, a preferred atomic ratio of rare earth promoter to copper is in the range of about 4 to 0.1 : 1, and even more preferred, 2 to 0.5 : 1. The term rare earth is used in its usual sense to describe the series often called the lanthanide series which includes La, Ce, Pr, Nd, Pm, Sm, Eu, Gd, Tb, Dy, Ho, Er, Tm, Yb and Lu. Compounds of these elements or mixtures thereof can be used as the promoter component of the catalyst. Suitable compounds would be the oxides, nitrates, sulfates, sulfites, phosphates, chlorides, etc. of the rare earth elements, e.g. lanthanum heptahydrate chloride, cerium carbonate, europium iodide, praseodymium acetate, neodymium chloride, samarium nitrate, europium chloride, gadolinium nitrate hexahydrate, terbium iodide, dysprosium selenate, holmium chloride, erbium nitrate, thulium bromide, ytterbium acetate, lutetium iodide and didymium oxide (Di = didymium is used here to describe a mixture of rare earths, e.g., a $Di_2O_3$ is typically 45 – 46 percent $La_2O_3$, 1 – 2 percent $CeO_2$, 9 – 10 percent $Pr_6O_{11}$, 32 – 33 percent $Nd_2O_3$, 5 – 6 percent $Sm_2O_3$, 3 – 4 percent $Gd_2O_3$, 0.4 percent $Yb_2O_3$ and 1 – 2 percent other rare earths).

The promoted copper catalyst can be prepared by a number of means all of which are conventional, for example, salts of copper and a rare earth promoter can be coprecipitated, or if insoluble or less soluble compounds are employed the components can be mixed in a slurry and subsequently dried. The catalyst can be prepared in any of the various forms known such as extruded pellets, cylinders or spheres, or they can be precipitated as powders or irregular particles. Alternatively, the catalyst can be ground or milled to a desired form. Another method of preparing the catalyst is to deposit them on to supports or carriers, such as alumina, silica alumina, silica gel, pumice, fire brick, etc.

In addition to the copper and rare earth components, other promoters, activators and stabilizers can be present, for example sulfur and phosphorus, alkali metal salts, e.g. sodium chloride, potassium chloride and lithium chloride.

The catalysts can be used without further treatment after preparation, however, greater activity and selectivity are noted when the catalysts are activated by heating at elevated temperatures, i.e., 600° – 1100° C. in a controlled atmosphere, e.g. air, nitrogen, helium, etc., for ¼ – 4 hours prior to use.

The feed for the present oxychlorination is a hydrocarbon, for example, methane, ethane, propane, butane, hexane, heptane, octane, decane, ethylene, propylene, butene, pentenes, butadiene-1,2, butadiene-1,3, cyclohexane, cyclooctane, cyclopentene, cyclohexene, cyclopentadiene, ethyl benzene, benzene, allene and the like. Aliphatic hydrocarbons are particularly suitable for the oxychlorination of the present invention, i.e., paraffin, olefin or acetylene. Generally, the feed will consist of aliphatic hydrocarbons of 1 to 30 carbons. The process is particularly useful for acyclic hydrocarbons having 2 to 12 carbon atoms, preferably $C_2 - C_4$.

The products of the present oxychlorinations will be as varied as the starting materials. The product will for the most part be a mixture of the chlorinated analogues of the hydrocarbon feed. Generally, mono and dichloro compounds predominate, however, there are substantial amounts of polychlorides and perchlorides, for example, in the case of an ethane feed, the products will be ethyl chloride, dichloroethane, vinyl chloride, other polychloro ethanes and ethylene. High temperatures are less favorable to chlorination and favor dehydrogenation. In some instances the mixed product is suitable for use as such, as for example, a general solvent. However, in most cases, it will be desirable to separate some or all of the various products. This can be achieved in a number of conventional ways, for example, distillation, fractional crystallization, solvent extraction, chromatographic extraction, selective reaction of one or more components or any combination of such conventional methods.

The oxychlorination reactions are generally carried out at elevated temperatures by passing a gaseous stream containing the hydrocarbon, oxygen and HCl through a bed of catalyst although other methods such as a fluidized catalyst bed can be employed, e.g. at 300° to 650° C. Under these conditions the hydrogen chloride is oxidized to chlorine and water. Since the reaction is highly exothermic no external application of heat is generally necessary, although heat may be applied initially to start the reaction. The particular preferential temperature within the permissible broad temperature range will vary to some extent with the nature of the catalyst and the hydrocarbon, necessitating somewhat higher or lower temperatures, e.g. 200° - 700° C. than generally applicable. In the present process it has been found that chlorine can be used to replace a portion or all of the hydrogen chloride with substantially the same results.

In a continuous process a convenient method of measuring hydrocarbon feed is in terms of the volume of hydrocarbon which contacts unit volume of catalyst composition per hour which is in units of reciprocal hours (hr$^{-1}$) and is commonly designated gaseous hourly space velocity (GHSV). The GHSV in the present process can be varied over a wide range of, for example, 25 to 600 GHSV. General indications are that the catalyst of the invention will give higher conversion at lower rates, i.e., GHSV <300 although some catalyst will exhibit substantially the same results at 50 and 400 GHSV. Lower conversions can be offset to some extent by the use of higher temperatures, however, there will normally be a reduction in selectivity to the organic chlorides with increased temperatures. Thus, the final selection of reaction conditions will depend on the value of high throughput to the operator and the degree of selectivity desired or the degree of non-selectivity that can be tolerated. Normally, the pressure will be atmospheric or somewhat less, however, the pressure can be adjusted as necessary for the operation of the process as previously indicated.

The hydrogen chloride is introduced into the system in substantially anhydrous form although it may contain small amounts of water. The oxygen can be introduced into the reaction zone as relatively pure oxygen or in a mixture such as in air. The mole ratio of oxygen to HCl is usually such as to sufficiently liberate the chlorine. Stoichiometrically, this can be derived from the equation:

$$4HCl + O_2 = 2Cl_2 + 2H_2O$$

However, in practice the mole ratio of oxygen to HCl can vary in the range of from .1 : 1 to 3 : 1. The mole ratio of hydrogen chloride to hydrocarbon will vary over a wide range of from .5 : 1 to 5 : 1 and more preferably .7 : 1 to 3 : 1.

In addition to oxygen, hydrogen chloride and hydrocarbon there can be present an inert diluent gas such as helium, argon, nitrogen or steam. When used, the diluent is generally present in a mole ratio of diluent to hydrocarbon in the range of from .5 : 1 to 20 : 1.

The process of the present invention can be carried out in any of the known types of conventional reactors, e.g. fixed bed, fluidized bed, Houdry flow, riser type and the like. Among the advantages of the present catalysts is high selectivity to the chlorinated hydrocarbons which in turn makes the process particularly suited to fixed bed reactors. The relatively low temperatures that can be employed allow the process to operate with a minimum of catalyst loss due to volatilization.

The following examples are presented to further illustrate the invention. Various methods of analysis and separation of product for identification were used including vapor phase chromatography, nuclear magnetic resonance and infrared. The examples were run in a one inch I.D. tubular Vycor* reactor, equipped with an external electric furnace. The reaction conditions and the active materials used are set forth in the specific examples. The hydrocarbon, oxygen, hydrogen chloride and diluent, if any, were added at the top of the reactor. The results are reported in mole percent conversion, selectivity and yield of the designated product. If not otherwise stated the catalysts were supported on Vycor rings. The catalysts compositions according to the invention have the copper component and a rare earth promoter component present in approximate equimolar quantities unless otherwise stated.

*Vycor is a trademark of Corning Glass Works - 96 percent silica, remainder being B$_2$O$_2$(glass)

EXAMPLES 1 - 5

These examples demonstrate the basic concept of the invention and show the improvement of the invention catalysts over the individual components. The conditions and results are set out in Table I. The results are set out as $$83 \begin{cases} 2.5/2.1 \\ 95/80 \\ 100/83 \end{cases}$$

for each run at the indicated temperatures. This indicates:

$$\text{mole \% conversion} \begin{cases} \text{selectivity/yield} \\ \text{(1) vinyl chloride} \\ \text{(2) vinyl chloride, ethyl chloride and dichloroethane} \\ \text{(3) total chlorinated product} \end{cases}$$

TABLE I

| Ex-ample | Catalyst | Feed[1] Composition | Molar Ratio | Conversion/Selectivity/Yield mole % at ° C. Temperature | | | |
|---|---|---|---|---|---|---|---|
| | | | | 300 | 350 | 400 | 450 |
| 1 | CuCO$_3$ | C$_2^-$/O$_2$/HCl/He | 1/0.5/2/2 | 83 {2.5/2.1, 95/80, 100/83} | 69 {6.7/4.6, 97/67, 100/69} | 80 {28/22, 76/1, 99+/80} | — |
| 2 | CeO$_2$ on AMC | C$_2^-$/O$_2$/HCl/He | 1/0.5/1/2 | 23 {0.4/0.1, 99+/23, 99+/23} | 22 {5.5/1.2, 91/20, 99/22} | 25 {16/4.0, 84/21, 98/24} | 33 {34/11, 77.25, 96/32} |
| 3 | " | C$_2$/O$_2$/HCl/He | 1/1/2/4 | — | — | 21 {14/2.9, 75/16} | 45 {29/13, 62/28} |

TABLE I-continued

| Example | Catalyst | Feed¹ Composition | Molar Ratio | Conversion/Selectivity/Yield mole % at °C. Temperature | | | | | | | |
|---------|----------|-------------------|-------------|---|---|---|---|---|---|---|---|
| | | | | 300 | | 350 | | 400 | | 450 | |
| 4 | $CuCO_3 \cdot CeO_2$ | $C_2^=/O_2/HCl/He$ | 1/0.5/2/2 | 72 | 0.3/0.2<br>99/71<br>99+/72 | 92 | 1.5/1.4<br>92/85<br>99+/91 | 87 | 96/20<br>1.2/1.0<br>72/63<br>99+/86 | 75 | 83/37<br>44/33<br>55/41<br>98/73 |
| 5 | $CuCO_3 \cdot CeO_2$<br>(1 hr at 900° C) | $C_2^=/O_2/HCl/He$ | 1/0.5/2/2 | 99 | 0.2/0.2<br>99+/98<br>100/99 | 99 | 1.0/1.0<br>96/95<br>100/99 | 96 | 1.2/1.2<br>71/68<br>99+/96 | 85 | 16/14<br>35/30<br>99/84 |

¹GHSV = 100
²AMC = 4 to 5 mesh alumina supports, Carborundum Company
³activated at 900° C. for 1 hour in air
$C_2^=$ = ethylene
$C_2$ = ethane It is readily apparent from Table I that the catalyst composition according to the present invention are superior to the individual components thereof.

EXAMPLES 6 – 8

These examples illustrate the use of a copper compound and a mixture of rare earth compounds. The conditions and results are reported in Table II. In these examples as well as Examples 9 – 19 the items within the $\{$ represent in order the mole % (selectivity/yield) of vinyl chloride
ethyl chloride
dichloroethane
other chlorinated compounds
ethylene (with ethane feed)*

* In runs with ethylene feed no ethylene product is reported.

The feed was ethane. The molar ratio of $C_2/O_2/HCl/He$ was 1/1/2/4 and GHSV = 100 in each run. Example 8 shows the use of ferric oxide promoted with the same mixture of rare earth compounds as Example 7. It can be seen that the conversion of Example 8 is not as good as Example 7 and that the iron atalyst produces a much higher yield of ethylene by-product.

TABLE II

| Ex. | Catalyst | Conversion/Selectivity/Yield, Mole % at Temperature °C. | | | | | |
|---|---|---|---|---|---|---|---|
| | | 300 | 350 | 400 | 450 | 500 | 550 |
| 6 | Didymium¹ Hydrate | | 25 { 4.0/1.0<br>77/19<br>tr./tr.<br>8.5/2.1<br>tr./tr. | 45 { 7.5/3.4<br>50/23<br>5.2/2.3<br>12/5.4<br>14/6.3 | 90 { 24/22<br>14/13<br>4.9/5.4<br>37/33<br>14/13 | 92 { 28/26<br>8.6/7.9<br>4.6/4.2<br>26/24<br>20/18 | 99 { 25/25<br>4.5/4.5<br>2.9/2.9<br>15/15<br>33/33 |
| 7 | [Didym. Hydr. $CuCO_3$] 1 hr. at 900° C.² | 82 { 15/12<br>26/21<br>22/18<br>22/18<br>5.3/4.3 | | 95 { 10/9.5<br>13/12<br>22/21<br>50/47<br>1.8/1.7 | 99 { 19/19<br>4.5/4.5<br>15/15<br>51/50<br>4.3/4.3 | 99 { 38/38<br>2.2/2.2<br>6.3/6.3<br>30/30<br>16/16 | — |
| 8 | [Didym. Hydr. $Fe_2O_3$ 1 hr. at 900° C.² | 25 { 1.9/0.5<br>1.9/0.5<br>10/2.5<br>5.7/1.4<br>14/3.5 | 39 { 4.2/1.6<br>65/25<br>5.8/2.3<br>18/7.0<br>3.7/1.4 | 83 { 10/8.3<br>26/22<br>11/9.1<br>31/26<br>16/13 | 96 { 20/19<br>15/14<br>8.3/8.0<br>29/28<br>19/18 | — | — |

¹Didymium - used to represent a mixture of rare earth compounds.
²Calcined in air for 1 hour at 900° C.

EXAMPLES 9 – 12

These examples all use a $CuCO_3 \cdot CeO_2$ (equimmolar) catalyst calcined in air for 1 hour at 900° C. and a GHSV of 100. The example shows the effects of varying the molar ratio of reagents and helium diluent. The feed was ethane held constant at one molar. The results are shown in Table III and are presented in the same manner as in examples 6 – 8.

TABLE III

| Example | Feed Composition | Molar Ratio | Conversion/Selectivity/Yield, Chromatogr. Mole % Temp. °C. | | | | |
|---|---|---|---|---|---|---|---|
| | | | 350 | 400 | 450 | 500 | 550 |
| 9 | $C_2/O_2/HCl/$ He | 1/0.25/1/1 | — | 20 { 1.0/0.2<br>61/12<br>32/6.4<br>5.5/1.1<br>tr./tr. | 50 { 3.3/1.7<br>22/11<br>34/17<br>32/16<br>3.9/2.0 | 34 { 4.8/1.6<br>11/3.7<br>24/8.3<br>20/6.7<br>32/11 | — |

TABLE III-continued

| Example | Feed Composition | Molar Ratio | Conversion/Selectivity/Yield, Chromatogr. Mole % Temp. °C. | | | | |
|---|---|---|---|---|---|---|---|
| | | | 350 | 400 | 450 | 500 | 550 |
| 10 | " | 1/0.25/2/1 | 38 { 2.4/0.9<br>12/4.7<br>50/19<br>30/11<br>tr./tr. | 53 { 2.0/1.0<br>6.1/3.2<br>40/21<br>41/22<br>3.3/1.8 | 44 { 17/7.4<br>2.5/1.0<br>23/10<br>48/21<br>5.1/2.2 | 41 { 20/8.1<br>2.8/1.1<br>26/11<br>29/12<br>14/5.9 | — |
| 11 | " | 1/0.5/2/4 | 41 { 1.0/0.4<br>45/18<br>40/16<br>10/4.1<br>tr./tr. | 72 { 2.8/2.0<br>15/11<br>57/41<br>23/17<br>tr./tr. | 88 { 7.4/6.5<br>3.5/3.1<br>47/42<br>29/26<br>7.4/6.5 | 88 { 28/24<br>2.4/2.1<br>0.8/0.7<br>22/20<br>41/36 | — |
| 12 | " | 1/1/2/4 | 30 { tr./tr.<br>7/21<br>21/6<br>7/2<br>tr./tr. | — | 96 { 8/8<br>5/5<br>25/24<br>36/34<br>6/6 | 99 { 5/5<br>1/1<br>25/25<br>44/44<br>3/3 | — |
| 13 | " | 1/1/4/4 | — | 19 { 1.6/0.3<br>77/15<br>14/2.7<br>6.9/1.3<br>tr./tr. | 92 { 6.4/5.9<br>26/24<br>22/20<br>36/33<br>4.5/4.1 | 83 { 10/8.3<br>16/13<br>16/13<br>33/27<br>21/18 | 92 { 17/16<br>4.0/3.7<br>9.4/8.7<br>28/26<br>8.4/7.7 |

EXAMPLES 14 – 16

These examples demonstrate the effect of varying the GHSV (50, 100, 400) on a particular catalyst and ratio of reagents. The catalyst was a $CuCO_3 \cdot CeO_2$ (equimolar) calcined in air for 1 hour at 900° C. The molar ratio of ethane/$O_2$/HCl/He was constant at 1/1/2/4 in each run. The results shown in Table IV indicate that for this catalyst and these ratios of reagents GHSV of 100 – 300 at 400° – 450° C. would be most suitable for the reduction of by-products such as ethylene.

EXAMPLES 17 – 21

These examples demonstrate a further improvement in the catalyst activity obtained with addition promoters. Example 15 is supplied as a comparison. In example 17, 2% by weight of 85% phosphoric acid was added to a $CuCO_3 \cdot CeO_2$ (equimolar) catalyst calcined 1 hour at 900° C. in air. Examples 18 and 19 show the use of 10% KCl as a second promoter. The results and conditions are given in Table V.

Example 20 and 21 show surprising results when 10% by weight of graphite (Fisher No. 38 graphite) and 10% by weight $PbCO_3$, respectively, are added to the copper-cerium catalyst.

TABLE IV

| Example | GHSV | Conversion/Selectivity/Yield. Chromatogr. mole % Temp. °C. | | | | | |
|---|---|---|---|---|---|---|---|
| | | 300 | 350 | 400 | 450 | 500 | 550 |
| 14 | 50 | — | 22 { tr./tr.<br>64/14<br>36/8.0<br>tr./tr.<br>tr./tr. | 64 { 6.2/4.0<br>17/11<br>51/32<br>16/10<br>4.9/3.1 | 70 { 11/7.7<br>5.0/3.5<br>11/7.7<br>15/12<br>51/36 | — | — |
| 15 | 100 | — | 41 { 1.0/0.4<br>45/18<br>40/16<br>10/4.1<br>tr./tr. | 72 { 2.8/2.0<br>15/11<br>57/41<br>23/17<br>tr./tr. | 88 { 7.4/6.5<br>3.5/3.1<br>47/42<br>29/26<br>7.4/6.5 | 88 { 28/24<br>2.4/2.1<br>0.8/0.7<br>22/20<br>41/36 | — |
| 16 | 400 | — | — | 6.5 { tr./tr.<br>63/4.1<br>28/1.8<br>9.2/0.6<br>0/0 | 49 { 8.3/4.1<br>31/15<br>23/11<br>12/6.0<br>24/12 | 51 { 11/5.6<br>24/12<br>9.7/4.9<br>10/5.1<br>40/20 | 52 { 10/5.2<br>13/6.9<br>2.1/1.1<br>3.1/1.6<br>58/30 |

TABLE V

| Ex. | Catalyst | Feed Composition | Molar Ratio | GHSV | Conversion/Selectivity/Yield, Chromatogr. mole % Temp., °C. | | | | |
|---|---|---|---|---|---|---|---|---|---|
| | | | | | 300 | 350 | 400 | 450 | 500 |
| | | | | | | 1.0/0.4<br>45/18 | 2.8/2.0<br>15/11 | 7.4/6.5<br>3.5/3.1 | 28/24<br>2.4/2.1 |

TABLE V-continued

| Ex. | Catalyst | Feed Composition | Molar Ratio | GHSV | Conversion/Selectivity/Yield, Chromatogr. mole % Temp., °C. | | | | |
|---|---|---|---|---|---|---|---|---|---|
| | | | | | 300 | 350 | 400 | 450 | 500 |
| 15 control | [CuCO$_3$ . CeO$_2$] 1 hr. at 900° C. | C$_2$/O$_2$/HCl/He | 1/1/2/4 | 100 | — | 41 { 40/16 ; 10/4.1 tr./tr. | 72 { 57/41 ; 23/17 tr./tr. | 88 { 47/42 ; 29/26 ; 7.4/6.5 | 88 { 0.8/0.7 ; 22/20 ; 41/36 |
| 17 | Copper-Cerium Cat. and 2% PO$_4$ heated to 700° Cw/Feed | C$_2$/O$_2$/HCl/He | 1/1/2/4 | 100 | 64 { 12/7.6 ; 11/6.9 ; 18/12 ; 49/32 ; 2.4/1.5 | 78 { 12/9.1 ; 9.5/7.4 ; 18/14 ; 52/41 ; 2.2/1.7 | 79 { 7.6/6.0 ; 12/9.6 ; 22/17 ; 51/41 ; tr./tr. | 94 { 13/12 ; 4.5/4.3 ; 15/14 ; 58/57 ; 2.0/2.0 | 98 { 20/19 ; 1.7/1/7 ; 7.5/7.3 ; 47/46 ; 5.8/5.7 |
| 18 | Copper-Cerium Cat. and 10% KCl | " | " | " 7.7 { 0/0 ; 100/7.7 ; 0/0 ; 0/0 ; 0/0 | 59 { 1.1/0.6 ; 62/37 ; 17/10 ; 13/7.9 ; 0/0 | 86 { 6.9/5.9 ; 17/15 ; 18/16 ; 46/39 ; 3.4/2.9 | 99 { 2.4/2.4 ; 3.0/3.0 ; 13/13 ; 70/69 ; 0.4/0.4 | 99 { 16/16 ; 0.4/0.4 ; 9.7/9.6 ; 47/46 ; 5.4/5.4 |
| 19 | " | C$_7^-$/O$_2$/HCl/He | 1/0.5/2/2 | " | 53 { tr./tr. ; 0/0 ; 97/51 ; 3.0/1.6 | 99 { 1.7/1.7 ; 0/0 ; 84/83 ; 1.3/1.3 | 98 { 12/11 ; 0/0 ; 46/45 ; 38/37 | 97 { 17/16 ; 0/0 ; 24/23 ; 41/40 | 75 { 32/24 ; 0/0 ; 6.0/4.5 ; 37/28 |
| 20 | [CuCo$_3$ . CeO$_2$] 1 hr. at 900° C + 10% PbCO$_3$ | C$_7^-$/O$_2$/HCl/He | 1/0.5/2/ | 100 | 93 { 1.4/1.3 ; 1.7/1.6 ; 85/79 ; 10/9.3 | — | 99 { 2.6/2.6 ; 0.2/0.2 ; 50/49 ; 45/44 | 70 { 28/20 ; 0.3/0.2 ; 18/13 ; 46/32 | 60 { 29/17 ; 0.5/0.3 ; 4.7/2.8 ; 51/31 |
| 21 | [CuCO$_3$ . CeO$_2$] 1 hr. at 900° C + 10% Fisher No. 38 Graphite | " | " | " | 86 { 3.3/2.8 ; 0.2/0.2 ; 87/75 ; 9.0/7.7 | 84 { 5.4/4.5 ; 0.2/0.2 ; 75/63 ; 19/16 | 85 { 25/21 ; 0.5/0.4 ; 38/32 ; 34/29 | 74 { 47/35 ; 0.7/0.5 ; 6.4/4.7 ; 40/30 | 70 { 66/46 ; tr./tr. ; tr./tr. ; 21/15 |

EXAMPLS 22-24

These examples show substantial variation of the molar ratio of copper component to rare earth component within the ranges previously recited does not have a substantial effect on the operation of the catalyst. The feed was butadiene (BD) principally the 1,3 isomers at a molar ratio of BD/O$_2$/HCl/He of 1/0.5/2/2 and GHSV of 100. The catalyst as CuCO$_3$. CeO$_2$. Each catalyst was calcined at 900° C. for 1 hour in air. The molar ratio of components is shown in the formulas in Table VI. The results are reported as before, i.e., conversion/selectivity/yield with the products being in order dichlorobutadiene
chlorobutene
chlorobutadiene.

TABLE VI

| Example | Catalyst | Conversion/Selectivity/Yield, Chromatogr. mole % Temp. °C. | | | | |
|---|---|---|---|---|---|---|
| | | 200 | 250 | 300 | 350 | 400 |
| 22 | [CuCO$_3$ . CeO$_2$] 1 hr. at 900° C. | — | — | 58 { 27/5 ; 9/2 ; 47/27 | 62 { 34/21 ; 11/7 ; 39/24 | 56 { 20/11 ; 8/5 ; 26/15 |
| 23 | [2CuCO$_3$ . CeO$_2$] 1 hr. at 900° C | 5 { 0/0 ; 0/0 ; 47/2 | 63 { 30/19 ; 12/8 ; 49/31 | 65 { 38/25 ; 14/9 ; 42/27 | 61 { 33/20 ; 13/8 ; 42/26 | — |
| 24 | [CuCO$_3$ . 2CeO$_2$] 1 hr. at 900° C. | — | 52 { 25/13 ; 10/5 ; 61/32 | 62 { 32/20 ; 12/7 ; 49/30 | 58 { 35/20 ; 14/8 ; 44/25 | 50 { 38/19 ; 15/8 ; 34/17 |

EXAMPLES 25 - 28

These examples demonstrate a further improvement in the chlorination of butadiene when a secondary promoter is present. The same conditions as in Examples 22-24 were employed. The results also reported as in Examples 22 - 24 in Table VII.

TABLE VII

| Example | Catalyst | Conversion/Selectivity/Yield, Chromatogr. mole % Temp. °C. | | | | |
|---|---|---|---|---|---|---|
| | | 200 | 250 | 300 | 350 | 400 |
| | | | | 27/5 | 34/21 | 20/11 |

TABLE VII-continued

| Example | Catalyst | Conversion/Selectivity/Yield, Chromatogr. mole % Temp. °C. | | | | |
|---|---|---|---|---|---|---|
| | | 200 | 250 | 300 | 350 | 400 |
| 22 | [CuCO$_3$ . CeO$_2$] 1 hr. at 900° C. | — | — | 58 { 9/2 47/27 | 62 { 11/7 39/24 | 56 { 8/5 26/15 |
| 25 | [CuCO$_3$ . CeO$_2$] 1 hr. at 900° C. + 10% LiCl | — | 9 { 0/0 0/0 49/4 | 67 { 26/17 10/7 50/34 | 63 { 36/23 13/8 41/26 | 41 { 32/13 13/5 29/12 |
| 26 | [CuCO$_3$ . CeO$_2$] 1 hr. at 900° C. + 10% NaCl | — | 27 { 16/4 5/1 52/14 | 67 { 33/22 11/7 46/31 | 63 { 38/24 13/8 41/26 | 44 { 35/15 13/6 28/12 |
| 27 | [CuCO$_3$ . CeO$_2$] 1 hr. at 900° C. + 10% KCl | 19 { 0/0 0/0 35/7 | 72 { 44/32 14/10 36/26 | 72 { 42/30 14/10 38/27 | 69 { 49/34 16/11 32/22 | — |
| 28 | [CuCO$_3$ . CeO$_2$] 1 hr. at 900° C. + 10% HgCl | — | 71 { 48/34 16/11 33/23 | 82 { 52/43 16/13 24/20 | 86 { 51/44 16/14 27/23 | — |

EXAMPLES 29 – 32

The molar ratio in the components of the feed was varied in relation to the butadiene. The GHSV was 100 in each run. Examples 29 and 30 and 1% KCl as addition promoter. A most noteworthy result is found in Examples 31 at 300° C. wherein there was a conversion of 90% and a yield of 51 mole % dichlorobutadiene. The variables and results are shown in Table VIII. The results are reported as in Examples 22 – 24.

EXAMPLES 33 – 35.

These examples demonstrate the very excellent results obtainable with steam as the diluent. The conditions and results (reported as in Exampls 22-24) are set in Table IX.

TABLE IX

| Ex. | Catalyst | Feed Composition | Molar Ratio | GHSV | Conversion/Selectivity/Yield. Chromatogr. mole % Temp. °C. | | | | | | |
|---|---|---|---|---|---|---|---|---|---|---|---|
| | | | | | 200 | 250 | 300 | 350 | 400 | 450 | 500 |
| 33 | CuCO$_3$ . CeO$_2$ 1 hr. at 900° C. | BD/O$_2$/-HCl/H$_2$O | 1/0.5/2/7 | 100 | — | — | — | 76 { 41/31 17/13 27/20 | 82 { 42/34 15/12 36/27 | 79 { 38/30 15/12 39/31 | — |
| 34 | " | BD/O$_2$/-HCl/H$_2$O | 1/1/4/7 | 125 | — | — | — | 56 { 41/23 15/8 26/11 | 75 { 43/32 20/15 23/17 | 81 { 48/39 20/16 24/19 | 73 { 38/28 17/12 34/25 |
| 35 | " | BD/O$_2$/-HCl/H$_2$O | 1/1/4/14 | " | — | — | — | — | 58 { 46/27 20/12 24/14 | 72 { 49/35 24/17 21/15 | 63 { 49/31 22/13 23/14 |

EXAMPLES 36 and 37.

These examples are provided to show that the diluent is not necessary for the successful operation of the oxychlorination using the present catalysts. Example 22 is supplied as a control. The GHSV was 100 for each run.

TABLE VIII

| Ex. | Catalyst | Feed Composition | Molar Ratio | Conversion/Selectivity/Yield, Chromatogr. mole % Temp., °C. | | | | | |
|---|---|---|---|---|---|---|---|---|---|
| | | | | 200 | 250 | 300 | 350 | 400 | 450 |
| 22 control | [CuCO$_3$ . CeO$_2$] 1 hr. at 900° C. | BD/O$_2$/HCl/He | 1/0.5/2/2 | — | — | 58 { 27/5 9/2 47/27 | 62 { 34/21 11/7 39/24 | 56 { 20/11 8/5 26/15 | — |
| 29 | " | BD/O$_2$/HCl/He | 1/0.5 2/10 | — | — | 30 { 12/4 5/2 56/17 | 56 { 28/16 9/5 55/31 | 47 { 24/11 9/4 53/25 | — |
| 30 | " + 1% KCl | BD/O$_2$/HCl/He | " | 10 { 0/0 0/0 5/0.5 | 53 { 14/7 4/2 65/34 | — | 78 { 37/29 13/10 45/35 | 67 { 32/21 11/7 52/35 | 48 { 23/11 9/4 48/23 |
| 31 | " | BD/O$_2$/HCl/He | 1/2/2/4 | 65 { 10/7 4/3 15/10 | — | — | — | 69 { 23/16 10/7 21/15 | 69 { 29/20 11/8 19/13 |
| 32 | " | BD/O$_2$/HCl/He | 1/1/2/4 | — | 56 { 54/30 19/11 19/11 | 90 { 57/51 21/19 15/13 | 87 { 42/37 15/13 36/31 | 85 { 45/38 18/15 27/23 | — |

The other conditions and results are reported in Table X.

TABLE X

| Ex. | Catalyst | Feed Composition | Molar Ratio | GHSV | *Conversion/Selectivity/Yield. Chrom. mole % Temp. °C. mole% | | | | |
|---|---|---|---|---|---|---|---|---|---|
| | | | | | 250 | 300 | 350 | 400 | 450 |
| 22 control | [CuCO₃ · CeO₂] 1 hr. at 900° C. | BD/O₂/-HCl/He | 1/0.5/2/2 | 100 | — | 58 { 27/5 9/2 47/27 | 62 { 84/21 11/7 39/24 | 56 { 20/11 8/5 26/15 | — |
| 36 | [CuCO₃ · CeO₂] 1 hr. at 900° C. | " | 1/1/4/0 | " | 22 { 40/8.8 12/26 23.5/1 | 78 { 46/36 17/13 24/19 | 69 { 45/31 18/12 24/17 | 68 { 45/31 17/12 28/19 | 68 { 38/26 16/11 28/19 |
| 37 | [CuCO₂ · CeO₃] 1 hr. at 900° C. + 5% KCl | " | 1/0.5/4/0 | " | — | 72 { 49/35 17/12 26/19 | 67 { 45/30 17/11 26/17 | — | — |

*Selectivities and yields to dichlorobutadiene-1,3, chlorobutenes and monochlorobutadiene-1,3, respectively, (top to bottom).

EXAMPLES 38 and 39.

Examples 38 and 39 show the oxychlorination of butene-1 and butene-2 respectively. The catalyst (equimolar CuCO₃ and CeO₃ calcined 1 hr. at 900° C. in air) and 5% KCl secondary promoter were deposited on 4 – 5 mesh alumina supports (AMC - Carborundum Company). The GHSV was 100 in each run and the ratio of hydrocarbon/O₂/HCl/He in each run was 1/0.5/2/2. The results are shown in Table XI.

EXAMPLE 40

This example demonstrates the operation of the process using chlorine substitute for HCl. This run is the same as Example 38 except for this substitution. The results are shown in Table XII. The results show a rather constant conversion, selectivity and yield over the temperature range of 150° – 350° C.

TABLE XII

OXYCHLORINATION OF BUTENE-1 and BUTENE-2 CHLORINE VS. HYDROGEN CHLORIDE

| Ex. | Catalyst | Feed Composition | Molar Ratio | GHSV | Products | Conversion/Selectivity/Yield, Chromatogr. Temp. °C. mole % | | | | |
|---|---|---|---|---|---|---|---|---|---|---|
| | | | | | | 150 | 200 | 250 | 300 | 350 |
| 40 | [CuCO₃ · CeO₂] 1 hr. at 900° C. + 5% KCl on AMC | Bu-1/O₂/-Cl₂/He | 1/0.5/-1/2 | 100 | *1,3-DiClBa 1,2-DiClBa 2,3-DiClBa 2-ClBD-1,3 Other Cₙ—Cl's | 70 { 1.4/1.0 97/68 0.1/0.1 1.1/0.8 0.1/0.1 | 70 { 1.4/1.8 95/70 tr./tr. 1.8/1.3 2.1/1.5 | 66 { 1.5/1.0 93/61 tr./tr. 2.1/1.4 2.9/1.9 | 70 { 12/8.4 71/50 tr./tr. 1.4/1.0 3.0/2.1 | 69 { 1.1/0.6 81/56 0.2/0.1 0.5/0.3 6.2/4.3 |

*1,3-DiClBa = 1,3-dichlorobutane
1,2-DiClBa = 1,2-dichlorobutane
2,3-DiClBa = 2,3-dichlorobutane
2-ClBD-1,3 = 2-chlorobutadiene No details of catalyst preparation have been given since the procedures involved require the preparation of an aqueous solution or slurry which is deposited onto the Vycor rings, which are then dried. Some of the catalysts are calcined as indicated prior to deposition, if any, on the supports. In any event, these procedures are

TABLE XI

| Examples | Catalyst | Hydrocarbon Feed | Products* | Conversion/Selectivity Yield, Chromatogr. Temp. °C. mole % | |
|---|---|---|---|---|---|
| | | | | 450 | 500 |
| 38 | [CuCO₃ · CeO₂] 1 hr. at 900° C. + 5% KCl on AMC | Butene-1 | 1-ClBD-1,3 2-ClBD-1,3 UNKNOWN, 1,3 DiClBa Other Cₙ—Cl's | 38 { 11/4.2 4.2/1.6 40/15 16/6.1 24/9.1 | — |
| 39 | " | Butene-2 | 1-ClBD-1,3 2-ClBD-1,3 UNKNOWN 1,3 DiClBa Other Cₙ—Cl's | 41 { 10.41 3.2/1.3 34/14 13/5.3 37/15 | 53 { 33/17 1.5/0.8 35/19 18/9.5 6.0/3.2 |

*1-ClBD-1,3 = 1-chlorobutadiene-1,3
2-ClBD = 2-chlorobutadiene-1,3
1,3 DiClBa = 1,3-dichlorobutanes

The invention claimed is:

1. In the process of oxychlorination of hydrocarbons comprising contacting in a vapor phase a hydrocarbon, hydrogen chloride or chlorine and oxygen at a temperature range of 200° – 700° C. in the presence of a catalyst wherein the improvement comprises employing a catalyst calcined at 600° – 1100° C consisting of a non-halide copper component consisting of copper and an element selected from the group consisting of O, S, N, P, As, Sn, Pb, Fe, Cr, Mo, W, V, Ti and mixtures thereof and a rare earth compound component, wherein the rare earth is selected from the group consisting of La, Ce, Pr, Nd, Pm, Sm, Eu, Gd, Tb, Dy, Ho, Er, Tm, Yb, Lu and mixtures thereof and the atomic ratio of rare earth to copper is in the range of 4 to 0.1:1.

2. The process according to claim 1 wherein said non-halide copper component is copper oxide, copper sulfate, copper nitrate, copper phosphate, copper arsenate, copper stannate, copper plumbate, copper ferrite, copper chromite, copper molybdate, copper tungstate, copper vanadate or copper titanate.

3. The process according to claim 1 wherein the atomic ratio of rare earth to copper is in the range of 2 to 0.5 : 1.

4. The process according to claim 1 wherein the rare earth component is a mixture of rare earths.

5. The process according to claim 1 wherein the catalyst is activated by heating at a temperature in the range of about 700° – 1100° C.

6. The process according to claim 1 wherein the mole ratio of hydrocarbon to hydrogen chloride to oxygen is in the range of 1 : 0.5 : 0.5 to 1 : 5 : 15.

7. The process according to claim 6 wherein a vaporous diluent is present in the mole ratio of diluent to hydrocarbon in the range of .5 : 1 to 20 : 1.

8. The process according to claim 1 wherein the hydrocarbon is an aliphatic hydrocarbon.

9. The process according to claim 8 wherein the aliphatic hydrocarbon has 1 to 30 carbon atoms.

10. The process according to claim 9 wherein the aliphatic hydrocarbon has 2 to 12 carbon atoms.

11. The process according to claim 1 wherein the rare earth is cerium.

12. The process according to claim 11 wherein the rare earth component is cerium oxide.

13. The process according to claim 12 wherein the copper component is copper oxide.

14. The process according to claim 13 wherein the catalyst is activated by heating at a temperature in the range of about 700° to 1100° C.

15. The process according to claim 14 wherein the mole ratio of hydrocarbon to hydrogen chloride to oxygen is in the range of 1 : 0.5 : 0.5 to 1 : 5 : 15.

16. The process according to claim 15 wherein a vaporous diluent is present in the mole ratio of diluent to hydrocarbon in the range of .5 : 1 to 20 : 1.

17. The process according to claim 16 wherein the hydrocarbon is an aliphatic hydrocarbon.

18. The process according to claim 17 wherein the aliphatic hydrocarbon has 1 to 30 carbon atoms.

19. The process according to claim 18 wherein the aliphatic hydrocarbon has 2 to 12 carbon atoms.

20. The process according to claim 16 wherein the hydrocarbon has 2 to 4 carbon atoms.

21. The process according to claim 20 wherein the hydrocaron is ethane.

22. The process according to claim 20 wherein the hydrocarbon is ethylene.

23. The process according to claim 20 wherein the hydrocarbon is butene.

24. The process according to claim 20 wherein the hydrocarbon is butadiene.

* * * * *